US008826587B2

(12) United States Patent
Baur et al.

(10) Patent No.: US 8,826,587 B2
(45) Date of Patent: Sep. 9, 2014

(54) METHOD FOR THINNING FRUIT

(75) Inventors: Peter Baur, Eppstein (DE); Wolfgang Benz, Burscheid (DE); Helmut Fürsch, Leichlingen (DE); Leonardo Pitta, Leverkusen (DE); Wolfgang Wirth, Bergisch Gladbach (DE); Michael Schröder, Unterwaldhausen (DE)

(73) Assignee: Bayer Cropscience AG, Monheim (DE)

( * ) Notice: Subject to any disclaimer, the term of this patent is extended or adjusted under 35 U.S.C. 154(b) by 163 days.

(21) Appl. No.: 10/487,979

(22) PCT Filed: Aug. 21, 2002

(86) PCT No.: PCT/EP02/09330
§ 371 (c)(1), (2), (4) Date: Feb. 27, 2004

(87) PCT Pub. No.: WO03/020034
PCT Pub. Date: Mar. 13, 2003

(65) Prior Publication Data
US 2004/0242425 A1 Dec. 2, 2004

(30) Foreign Application Priority Data
Sep. 3, 2001 (DE) .................... 101 43 084

(51) Int. Cl.
*A01B 41/00* (2006.01)
*A01N 43/707* (2006.01)

(52) U.S. Cl.
CPC ................... *A01N 43/707* (2013.01)
USPC ......................................... 47/1.43

(58) Field of Classification Search
USPC ............... 47/58.1 FV, 58.1 R, 1.43; 504/212
See application file for complete search history.

(56) References Cited

U.S. PATENT DOCUMENTS

2004/0242425 A1 * 12/2004 Baur et al. ............ 504/212

FOREIGN PATENT DOCUMENTS

| JP | 2001-206803 | * | 7/2001 | ............ A01N 37/02 |
| WO | WO 03020034 A1 | * | 3/2003 | ............ A01N 43/707 |

OTHER PUBLICATIONS

Gilreath et al. Jul. 2001. Crop injury from sublethal rates of herbicide. I: Tomato. HortScience 36(4): 669-673.*
Gilreath et al. Jul. 201. Crop injury from sublethal rates of herbicide. III: Pepper. HortScience 36(4): 677-681.*
Veerman. 1998. Prevention of erry set and true seed production in six potato (Solanum tuberosum L) cultivars by single foliar applications of MCPA. Potato Research 41(2): 127-133.*
Van Oorschot et al. 1978. Recovery from inhibition of photosynthesis by metamitron in various plant species. Weed Research 19: 63-67.*
Faculty of Horticulture Annual Report 1995, published in Warsaw Agricultural University—SGGW Warsaw 1996, p. 11, W. Guzewski, "Further studies on chemical thinning of apples".
R.E. Byers et al.: "Apple thinning by photosynthetic inhibition" J. Amer. Soc. Hort. Sci., Bd. 115, Nr. 1, 1990, Selten 14-19, XP001120641.

* cited by examiner

*Primary Examiner* — Monica Williams
(74) *Attorney, Agent, or Firm* — Miles & Stockbridge P.C.

(57) ABSTRACT

The present invention relates to a method for thinning fruit by using the active substance metamitron and corresponding metamitron-containing fruit thinning formulations.

12 Claims, No Drawings

METHOD FOR THINNING FRUIT

The present invention relates to a method for thinning fruit using metamitron-containing thinning formulations.

Economically speaking, thinning is widely considered to be the most important measure in pome fruit growing and in the commercial cultivation of a large number of other fruit crops. Thinning is understood as meaning the reduction in number of the pollinated flowers or of the number of fruit by mechanical means (by machine or hand) or by chemical agents. Advantages achieved through thinning are an improved fruit size, color and/or quality together with a substantially improved profitability, the improvement of flowering in the year following prolific flowering, or breaking and preventing biennial bearing in endangered varieties and young plantations, and avoiding the breaking of overloaded branches, pronounced exhaustion of the tree and the concomitant reduced low-temperature resistance of the tree.

Thinning by hand is not an option in most growing regions owing to the costs involved. Thinning with machines is possible to a limited extent only, owing to, inter alia, the difficulty of combining efficacy with avoiding damage to the tree, as far as this is possible, owing to the sensitivity of varieties/trees and owing to the necessity of training the trees into particular shapes (cultivation method).

This is why chemical thinning is of great importance. However, chemical thinning agents which are currently used, such as urea and ammonium thiosulfate (which are not licensed in Germany for this purpose) are not very satisfactory with regard to their reliability and are frequently poorly tolerated by the plants at the concentrations used, which need to be high. Other thinning agents which have not been licensed in Germany to date or which are no longer licensed in Germany, too, are not entirely suitable for practice conditions with regard to their efficacy and plant tolerance since a very pronounced, variety-dependent lack of reliability, which is influenced by the developmental stage of the fruit (flower) and the climatic conditions during and after the application, has always been observed. All of these known thinning agents act via the hormone balance of the plant (for example action via the plant hormones auxin and ethylene in apples). The result is that undesired effects are frequently observed with the formulations, such as, for example, a reduced action at low concentrations, an unduly high degree of thinning under adverse conditions at the time of application or in some cases indeed promotion of cropping. In addition, the agents from the carbamate group, which are employed in many countries, only have a limited use as insecticide.

The use of photosynthesis-inhibiting active substances for fruit thinning has been described in J. Amer. Soc. Hort. Sci. 115(1): 14-19 (1990). The photosynthesis-inhibiting active substances stated therein have, however, not been used commercially as thinning agents since their plant tolerance is unsatisfactory (for example in the case of metribuzin). W. Guzewski has studied the use of the photosynthesis-inhibiting active substance metamitron (published in Warsaw Agricultural University- SGGW, Faculty of Horticulture, Annual Report 1995, Warsaw 1996). According to this paper, spraying a "Golden Delicious" apple variety with metamitron 7 days post-flowering at an application rate of 500 mg/l and 700 mg/l resulted in an increased fruit weight of 150 and 180 g, respectively, in comparison with a standard (98 g). However, this method has not gained commercial importance as yet. The reason appears to be that plant damage (foliar necroses) can be observed at the application rates described, and, when the circumstances are unfavorable, an unduly high degree of thinning, which entails yield losses, occurs. Moreover, owing to the early application window (7 days post-flowering), the method is a floral thinning method.

Several years after Guzewski's publication, it has now been found, surprisingly, that efficient fruit thinning (as opposed to floral thinning) which avoids plant damage can be effected when a ready-to-use thinning formulation (for example a spray mixture) comprising 50-400 mg/l metamitron is applied to the plant organs, in particular the fruits. In contrast to application rates of 700 mg/l, no unduly high degree of thinning, which entails yield losses, and no foliar necroses are observed. No, or barely discernable, damage to the crop plants is observed. The formulations are therefore well tolerated by plants. In addition, the method according to the invention avoids biennial bearing in the plantations.

A late fruiting stage is understood as meaning, in this context, in particular application at a later fruiting stage, preferably the 8 to 30 mm, especially preferably the 8 to 17 mm, especially preferably the 10 to 12 mm, fruiting stage or later. This procedure permits the selective thinning of fruit after observing the actual cropping level up to as late as including June drop. Such a method for efficiently thinning fruit at a late stage without damaging the plants has not been known to date.

The method according to the invention employs read-to-use fruit thinning formulations comprising 150-400 mg/l metamitron, which are novel and likewise subject-matter of the present application.

The ready-to-use thinning formulations according to the invention preferably comprise 150-375 mg/l, very especially preferably 200-350 mg/l, metamitron, a metamitron content of 350 mg/l being considered as ideal for most purposes.

The fruit thinning formulations according to the invention are advantageously prepared as water-based formulations.

In addition to metamitron, the fruit thinning formulations according to the invention also comprise, if appropriate, additives, other thinning agents, growth regulators, foliar fertilizers and agrochemical active substances.

Suitable additives which may be present in the thinning formulations according to the invention are further agrochemical active substances and also crystallization inhibitors, wetters, emulsifiers or else water.

Suitable crystallization inhibitors which may be present in the thinning formulations according to the invention are all substances which can conventionally be employed for such purposes in agrochemical compositions. The following may be mentioned by way of preference: N-alkylpyrrolidones such as N-octylpyrrolidone and N-dodecylpyrrolidone, furthermore copolymers of polyvinylpyrrolidone and polyvinyl alcohol such as, for example, the polyvinylpyrrolidone/polyvinyl alcohol copolymer which is known under the name Luviskol VA 64® (BASF), furthermore dimethylamides of alkylcarboxylic acids such as dimethyldecanamide, or the $C_{6-12}$-alkanecarboxylic acid dimethylamide mixture which is known under the name Hallcomid® (Hall Comp.), and furthermore copolymers of ethylenediamine with ethylene oxide and propylene oxide, such as, for example, the product known under the name Synperonic® T 304 (Uniqema).

Suitable wetters are all the substances which can be employed for such purposes in thinning formulations. The following may be mentioned by preference: alkylphenol ethoxylates, dialkylsulfosuccinates, such as sodium dioctylsulfosuccinate, lauryl ether sulfate and polyoxyethylene sorbitan fatty acid esters. The use of silicone surfactants as wetters may be mentioned in particular.

Suitable emulsifiers are all the customary nonionic, anionic, cationic and zwitter-ionic substances with surface-active properties which are conventionally employed in agrochemical compositions. These substances include reaction products of fatty acids, fatty acid esters, fatty alcohols, fatty amines, alkylphenols or alkylarylphenols with ethylene oxide and/or propylene oxide, and their sulfuric esters, phosphoric acid monoesters and phosphoric acid diesters, furthermore reaction products of ethylene oxide and propylene oxide, moreover alkylsulfonates, alkyl sulfates, aryl sulfates, tetraalkylammonium halides, trialkylarylammonium halides and alkylaminesulfonates. The emulsifiers can be employed individually or else as a mixture. Emulsifiers which may be mentioned by preference are reaction products of castor oil with ethylene oxide in a molar ratio of 1:20 to 1:60, reaction products of $C_6$-$C_{20}$-alcohols with ethylene oxide in a molar ratio of 1:5 to 1:50, reaction products of fatty amines with ethylene oxide in a molar ratio of 1:2 to 1:20, reaction products of 1 mol of phenol with 2 to 3 mol of styrene and 10 to 50 mol of ethylene oxide, reaction products of $C_8$-$C_{12}$-alkylphenols with ethylene oxide in a molar ratio of 1:5 to 1:30, alkylglycosides, salts of $C_8$-$C_{16}$-alkylbenzenesulfonic acids, such as, for example, calcium salts, monoethanolammonium salts, diethanolammonium salts and triethanolammonium salts.

Examples of nonionic emulsifiers which may be mentioned are the products known under the names Pluronic® PE 10 100 (BASF) and Atlox® 4913 (Uniqema). Others which are suitable are tristyrylphenol ethoxylates. Examples of anionic emulsifiers which may be mentioned are the product from Bayer AG which is commercially available under the name Baykanol® SL (=condensate of sulfonated ditolyl ether and formaldehyde) and phosphated or sulfated tristyrylphenol ethoxylates, with Soprophor SLK® and Soprophor® 4D 384 (Rhodia) being mentioned individually.

Other thinning agents which can be added to the thinning formulations according to the invention and which may be mentioned are carbaryl, 2-(1-naphthyl)acetic acid (NAA), benzyladenine, naphthyloxyacetic acid (NEA), gibberillic acid, paclobutrazole, ammonium thiosulfate and urea, and ethylene generators such as ethephon in apple varieties where thinning is difficult or which tend to biennial bearing, such as Elstar or Red Delicious. Thinning formulations according to the invention which comprise ethephon in addition to metamitron must be emphasized for the use of the thinning formulations according to the invention in those crops where thinning is difficult. In such a case, the thinning formulations advantageously comprise 100 to 1000 mg/l ethephon.

A growth regulator which can optionally be added and which may be mentioned by way of example is prohexadione-calcium.

The addition, to the thinning formulations according to the invention, of foliar fertilizers, plant protection agents or plant strengthening agents is especially advantageous. Those which may be mentioned are: calcium salts such as calcium chloride, calcium nitrate and their formulations (for example Düngal®, Wuxal®, Basfoliar®, Bayfolan®), ammonium thiosulfate, ammonium nitrate, urea, iron chelates, magnesium sulfate and trace minerals such as boron, zinc, manganese and the like, with urea being emphasized as particularly advantageous addition.

The use of calcium formate as foliar fertilizer in the fruit thinning formulations according to the invention should be particularly emphasized. Calcium formate is especially inexpensive to purchase and avoids problems associated with the calcium salts conventionally used in agrochemical formulations. Thus, for example, calcium formate is not hygroscopic or contaminated by alkaline impurities ($Ca(OH)_2$), as is the case with commercially available $CaCl_2$, where, indeed, intolerance symptoms were observed when young plants were sprayed directly; it is also less sparingly soluble in water than $CaCO_3$. Moreover, the new calcium-formate-comprising formulations have better rainfastness than the conventionally used calcium salts (nitrate, carbonate and chloride).

Like the other calcium salts, the calcium formate which is applied, preferably sprayed, together with the thinning formulations according to the invention onto young plant organs (leaves and fruits) is highly suitable for avoiding calcium deficiency symptoms in the plants and above all the fruits (for example bitter pit in apples) (see, for example, Japanese Patent Specification No. J04-202080). Surprisingly, calcium formate is also particularly easy to formulate, and plant intolerance symptoms were not observed.

The thinning formulations according to the invention therefore preferably comprise 0.1 to 50 g/l (0.01-5% by weight) of calcium formate, a calcium content of 1 to 20 g/l being especially preferred.

Agrochemical active substances which can additionally be added to the thinning formulations according to the invention are, for example, fungicides and insecticides, depending on the application in question.

Examples of fungicides which may be mentioned are sulfur (wettable sulfur), copper preparations, benzimidazole, bitertanol, dichlofluanid, fenarimol, fenhexamid, fludioxonil, fosetyl-aluminum, iprodione, myclobutanil, penconazole, triadimenol, vinclozolin, tolylfluanid (Euparen M®), captan, propineb, trifloxystrobin, kresoxim-methyl, dithianon, cyprodinil, pyrimethanil, mancozeb (Dithane Ultra®) and metiram, with tolylfluanid being especially emphasized.

Examples of insecticides which may be mentioned are dimethoate, oxydemeton-methyl, malathion, parathion-methyl, phosphamidon, permethrin, amitraz, clofentezin, cyhalothrin, beta-cyfluthrin, fenproximate, diflubenzuron, tebufenozide, imidacloprid, thiacloprid, thiametoxam, clofentezine, fenoxycarb, parathion-methyl, XenTari®, tebufenozide, diflubenzuron, pirimicarb, tebufenpyrad, fenpyroximate, rapeseed oil, mineral oil and lecithin, with imidacloprid and thiacloprid being especially emphasized.

The thinning formulations according to the invention are prepared in such a way that the components are mixed with each other in the ratios desired in each case.

In the preparation of the thinning formulations according to the invention, the temperatures can be varied within a certain range. In general, they are prepared at temperatures between 10° C. and 50° C., preferably at room temperature.

For the purpose of their application, the thinning formulations according to the invention are advantageously prepared from WP, WG, SL and SC formulations of the active substances and additives by dissolving the formulation in a solvent, preferably water. Application is effected by customary methods, for example by spraying, pouring, atomizing, injecting, painting of the emulsions, suspensions, solutions or aerosols prepared.

The application rate of water for the thinning formulations according to the invention can be varied within a substantial range. It depends in each case on the active substances present and on their concentration in the formulations. An application rate of 500 to 1500 l/ha is thought of as preferred. As a rule, the application rate for the thinning formulations according to the invention is 1000 l/ha. However, lower water application rates of 100 to 300 l may also be employed in certain cultivation methods.

This means that, ideally, 0.05 to 0.4 kg/ha (preferably 0.1 to 0.375 kg/ha, especially preferably 0.2 to 0.35 kg/ha) of metamitron is applied in the method according to the invention.

Conventional equipment employed for preparing agrochemical formulations is suitable for the preparation of the thinning formulations according to the invention.

However, the formulations according to the invention can not only be used for thinning fruit in the method according to the invention, but can, depending on the circumstances, be used as early as from the flowering period (floral thinning).

In the method according to the invention, application to the plant organs is advantageously carried out by spraying the formulations according to the invention. In this case, the plant organs, in particular the leaves or fruits, are sprayed directly.

The uptake of calcium from the calcium-formate-comprising formulations according to the invention is particularly efficacious at the early spraying dates conventionally used for thinning.

The method according to the invention is particularly suitable for thinning fruit in pome fruit crops. Crops and varieties which may be explicitly mentioned are: all apple varieties (for example Boskoop, Braeburn, Cox Orange, Elstar, Gala, Gloster, Golden Delicious, Fuji, Jamba, James Grieve, Jonagold, Jonathan, Lobo, McIntosh, Red Delicious, Spartan), all pear varieties (for example Conference), quince and Asiatic pear. There is also a suitability for the stone fruit crops peach and plum, and for olive, pistachios, kiwi fruit, grapevines or citrus crops (for example tangerines).

The invention is illustrated by the examples which follow.

EXAMPLES

Thinning Formulations

A given amount of metamitron is mixed with the desired amounts of additives (for example urea, silicone surfactants) and made up to the desired concentration with water. The standards are likewise prepared by dissolving the commercially available active substances in water.

Thus, for example, the following thinning formulations were prepared.

Formulation 1 (In Accordance with the Invention)

Aqueous spray mixture comprising 350 mg/l metamitron, 9 g/l urea, 60 mg/l of a silicone surfactant.

Formulation 2 (In Accordance with the Invention)

Aqueous spray mixture comprising 350 mg/l metamitron, 2 g/l urea.

Formulation 3 (Not in Accordance with the Invention, Only Moderately Tolerated by Plants)

Aqueous spray mixture comprising 700 mg/l metamitron, 2 g/l urea.

Formulation 4 (Not in Accordance with The Invention, Standard)

Aqueous spray mixture comprising 350 mg/l metamitron.

Formulation 5 (Not in Accordance with the Invention, Standard)

Aqueous spray mixture comprising 800 mg/l Amid-Thin® and 300 mg/l ethephon.

Formulation 6 (Not In Accordance with the Invention, Standard)

Aqueous spray mixture comprising 850 mg/l carbaryl (Sevin®).

Biological Action

The following thinning results were obtained for the abovementioned formulations in spraying experiments on apples cv. Golden Delicious in the production region "Altes Land" (Germany).

TABLE

Result of the intermediate assessment after June drop for the effect of metamitron formulations on the thinning of Golden Delicious (Altes Land). Water application rate: 1000 l/ha.

| No. | Variant | Active compound concentration | Cropping (% of the control) |
|---|---|---|---|
| 1 | Control | — | 100 |
| 2 | Formulation 1 | 350 ppm | 76 |
| 3 | Formulation 2 | 350 ppm | 82 |
| 4 | Formulation 3 | 700 ppm | 85 |
| 5 | Formulation 4 | 350 ppm | 112 |
| 6 | Formulation 5 | 800 + 300 ppm | 106 |
| 7 | Formulation 1 | 350 ppm | 42 |
| 8 | Formulation 2 | 350 ppm | 33 |
| 9 | Formulation 3 | 700 ppm | 36 |
| 10 | Formulation 4 | 350 ppm | 41 |
| 11 | Formulation 6 | 850 ppm | 70 |

No. 2–6: Floral thinning
No. 7–11: Fruit thinning

The data show that the formulations according to the invention demonstrate superior thinning in comparison with the standards. This advantageous thinning effect is even more pronounced at the later application during the 10-12 mm fruit stage.

Plant Tolerance

According to visual scoring, formulations comprising 350 mg/l metamitron show no or only minimal damage when used in thinning experiments on a wide range of apple varieties, while formulations comprising 700 mg/l metamitron cause minimal to clearly discernable damage under identical conditions.

We claim:

1. A method for thinning fruits of apples or pears comprising applying at a later fruiting stage of 8 to 30 mm fruit size a thinning formulation comprising 50 to 400 mg/l metamitron to plant organs.

2. The method of claim 1 wherein said thinning formulation is applied at a rate of 0.05 to 0.4 kg/ha metamitron to plant organs.

3. The method of claim 1 wherein the thinning formulation comprises 100 to 375 mg/l metamitron.

4. The method of claim 3 wherein the thinning formulation comprises 150 to 375 mg/l metamitron.

5. The method of claim 1 wherein the thinning formulation further comprises 0.1 to 50 g/l calcium formate.

6. The method of claim 5 wherein the thinning formulation comprises 1 to 20 g/l calcium formate.

7. The method of claim 1 wherein the later fruiting stage is an 8 to 17 mm fruit size.

8. The method of claim 7 wherein the later fruiting stage is a 10 to 12 mm fruit size.

9. The method of claim 1, wherein no or only minimal foliar necroses are observed in the method for thinning fruits.

10. The method of claim 1, wherein no foliar necroses are observed in the method for thinning fruits.

11. A fruit thinning formulation, comprising 50 to 400 mg/l metamitron and 0.1 to 50 g/l calcium formate.

12. The fruit thinning formulation as claimed in claim 11, comprising 1 to 20 g/l calcium formate.

* * * * *